(12) United States Patent
Lan

(10) Patent No.: US 6,217,880 B1
(45) Date of Patent: Apr. 17, 2001

(54) MEDICAMENT FOR TREATING RECURRENT ULCER OF MOUTH AND BEHCET'S SYNDROME

(76) Inventor: Jinchu Lan, Floor 8, Building No. 10, Nanxiange, Xuanwu District, Beijing City (CN), 100053

( * ) Notice: Subject to any disclaimer, the term of this patent is extended or adjusted under 35 U.S.C. 154(b) by 0 days.

(21) Appl. No.: 09/509,331
(22) PCT Filed: Dec. 28, 1998
(86) PCT No.: PCT/CN98/00315
§ 371 Date: May 23, 2000
§ 102(e) Date: May 23, 2000
(87) PCT Pub. No.: WO00/06181
PCT Pub. Date: Feb. 10, 2000

(30) Foreign Application Priority Data

Jul. 24, 1998 (CN) .............................. 98 103 423

(51) Int. Cl.⁷ .......................... A01N 65/00; A61K 35/78; A61K 39/385
(52) U.S. Cl. ......................................... 424/195.1; 514/925
(58) Field of Search .......................... 424/195.1; 514/925

Primary Examiner—Leon B. Lankford, Jr.
Assistant Examiner—Michele Flood
(74) Attorney, Agent, or Firm—Bromberg & Sunstein LLP

(57) ABSTRACT

This invention relates to a medicament for treating recurrent ulcer in mouth and Behcet's syndrome, which can be prepared mainly from root of *Coptis chinesis*, Isatis root, flower of lonicera, puccoon, dried rhemannia, lily bulb, bamboo leaf, *Coydalis bungeana,* Chinese wild ginger and snake gallbladder, and optionally ganoderma and thunder god vine in certain weight proportions. It can be formulated into any common dosage form. The medicament of the invention has the effect of clearing heat and draining fire, diminishing inflammation, antibiosis, cooling blood and closing sores, etc., which is an effective medicament of empolying widespreadly, producing a rapid effect and high cure rate.

17 Claims, No Drawings

MEDICAMENT FOR TREATING RECURRENT ULCER OF MOUTH AND BEHCET'S SYNDROME

TECHNICAL FIELD

The present invention relates to a medicament for treating recurrent ulcer in mouth and also relates to a medicament for the treatment of Behcet's Syndrome, which belongs to the field of traditional Chinese medicine.

BACKGROUND OF THE INVENTION

Recurrent ulcer in mouth is one kind of common stomatopathy, which is clinically characterized by solitary round or elliptic shallow aphtha occuring repeatedly in the oral mucosa. It frequently influences the patient's eating, drinking and sleeping due to severe spontaneous pain when attacking. In western medical therapy method it is treated by topically administering and orally taking vitamins B1, B2 and C simultaneously, and the serious ulcer can be treated by orally administering hormones for a short period. In traditional Chinese medical therapy the Chinese medicine prescription is determined by identifying deficient or excessive syndrome and based on causes of disease and clinical symptoms; however, few oral Chinese patent medicine preparations produced and developed in view of deficient or excessive syndrome have been found. Traditional preparations for external use, such as Xilei San(Xilei Powder), Bingpeng San(Borneol and Boraxg Powder), and oral preparations, such as Niuhuangjiedu Wan(Bovine Bezoar Toxin-resolving Pill) and Shangqing Wan (Bovine Bezoar Upper-Body-Cleaning Pill), only cure ulcer but not clear the potential cause of the disease, so that the problem of recurrence of the disease can't be solved radically.

DETAILED DESCRIPTION OF THE INVENTION

The object of the present invention is to provide a Chinese medicament which can be used for treatment of recurrent ulcer in mouth and Behcet's syndrome effectively.

The medicament of the present invention could be prepared from the following raw material herbs in weight proportions below (by weight portions):

| | |
|---|---|
| root of Coptis chinesis | 6–9 portion |
| Isatis root | 2–5 portion |
| flower of Lonicera | 2–5 portion |
| Puccoon | 2–4 portion |
| root of dried Rehmannia | 3–8 portion |
| bamboo leaf | 3–6 portion |
| Corydalis bungeana | 2–5 portion |
| Chinese wild ginger | 2–4 portion |
| Lily bulb | 2–5 portion |
| dried powder of snake gallbladder | 0.1–0.5 portion |

The medicament of the present invention could be prepared preferably by the following raw material herbs in weight proportions (by weight portions):

| | |
|---|---|
| root of Coptis chinesis | 7.5 portion |
| Isatis root | 4.5 portion |
| flower of Lonicera | 4.5 portion |
| puccoon | 3 portion |
| root of dried Rehmannia | 6 portion |
| bamboo leaf | 4.5 portion |
| Corydalis bungeana | 4.5 portion |
| Chinese wild ginger | 3 portion |
| Lily bulb | 4.5 portion |
| dried powder of snake gallbladder | 0.3 portion |

The medicament of the present invention may be prepared from the above mentioned raw material herbs in said weight proportions and, additionally, 3-8, preferably 6, weight portions of Ganoderma (*Ganoderma japonicum*) and 1-3, preferably 1.5, weight portions of thunder god vine (*Tripterygium wifordii*). The added herbs can restore health and eliminate pathogens and enhance curative effect.

The medicament of the invention may be prepared from above formulation of raw material herbs by conventional Chinese medicine preparation method into common forms, such as pills, powders, tablets, oral liquids, creams. While preparing the medicament of the invention, conventional assistant additives, such as starch, can be also added into above raw material herbs.

The medicament of the present invention may be prepared by following method:

The seven raw materials, bamboo leaf (lophatherum), root of *Coptis chinesis,* Isatis root (*Isatis tinctoria* L.), flower of lonicera (honeysuckle flower; *Lonicera japonica* Thunb), *Corydalis bungeana,* Lily bulb and root of dried Rehmannia (*Rhemannia glutinosa*), in the above mentioned portions are decocted twice with water, in which certain amount of water is added until the surface of the raw material herbs is just submerged each time. Two decoction liquids obtained above are combined, and then filtered to yield filter liquor 1. Chinese wild ginger (*Asarum sieboldii; Asarum hetrotropoids manshuricum*) in the said portions is extracted with water by a common extraction method, volatile oil is collected for later use and then the decoction liquid is combined with the filter liquor 1, and concentrated into an extractum which specific gravity may be 1.35. The extractum is added with 90–95% ethanol. The ethanol solution is concentrated whiling recovering ethanol and dried at 45–50° C. to yield dried extractum 1. Puccoon (Purple gromwell) in said portions is extracted with 90–95% ethanol under reflux, and the extracted liquor is concentrated while recovering ethanol and dried at 45–50° C. to obtain dried extractum 2. Dried extractum 2 is combined with dried extractum 1, and then grinded into powder. Into the powder yielded the dried powder of the snake gallbladder with the said weight proportion is added, and then further grinded into fine powder. The common assistant additives is added into said fine powder. The mixture of the assistant additives and said fine powder are prepared into granule, dried, sprayed with the volatile oil of Chinese wild ginger obtained above, and then prepared into tabletes by tabletting.

The ganoderma and thunder god vine of said portions may be further added into above raw material herbs to prepare the medicament of the invention which can restore health and eliminate pathogens and enhance curative effect.

The medicament of the invention has the effect of eliminating heat and clearing fire, diminishing inflammation, antibiosis, cooling blood and closing sore, etc., which can be used to treat recurrent ulcer in mouth and Behcet's Syndrome.

In the medicament of the invention the root of Coptis chinesis is used as the sovereign component, which with cold nature and bitter flavour, enters heart, liver, stomach and large intestine meridian, and has the effect of clearing heat, drying dampness, draining fire, especially eliminating excessive heat in heart and stomach, removing toxin, and curing sore-toxin. The root of Coptis chinesis is chosen as the sovereign component, for it treats accumulated heat in heart and spleen and cures sore.

The Corydalis bungeana, the Isatis root and puccoon are used as the ministerial components in the invention. Corydalis bungeana with cold nature and acrid and bitter flavour enters heart and spleen meridian, and has the effect of clearing heat and removing toxin. Due to its discharging effect of bitterness, dissipating effect of acridity, and clearing heat of cold nature, it is used for treating stagnation of blood and heat, red-swelling, heat-pain, and swelling and pain of sore-toxin. Isatis root with cold nature and bitter flavor enters heart and stomach meridian and has the effect of clearing heat, removing toxin, cooling blood and nourishing throat, which is used for the treatment of fever, headache, swelling sore in throat, swollen and painful sore-toxin. Puccoon with cold nature and sweet flavor enters heart and liver meridian and has the effect of cooling blood, activating blood, removing toxin and releasing pain, which is used for the treatment of hot blood, accumulated toxin and swollen and painful sores. These three herbs with the effect of clearing heat, removing toxin and cooling blood combine together to assist the effect of sovereign component, the root of Coptis chinesis, on heat-clearing, toxin-resolving and sore-treating, as ministerial components.

In the medicament of the invention, flower of lonicera, bamboo leaf, snake gallbladder, root dried Rhemannia and the lily bulb are used as adjuvant components. Flower of lonicera with cold nature and sweet flavor enters lung, heart and stomach meridian and has the effect of clearing heat, removing toxin, dissipating wind and heat, releasing pain and dispersing swelling, which is an important component for treatment of swollen and painful sores. Bamboo leaf with cold nature and bland, acrid and sweet flavor enters heart, stomach and small intestine meridian and has the effect of clearing heat, eliminating vexation, engendering liquid and inducing diuresis. Clearing heart fire results in removing heat, relieving small intestine results in inducing diuresis, and moving down heart fire leads to clean urine. Therefore, bamboo leaf is used for the treatment of up-flaming heart fire and sore mouth and tongue. Snake gallbladder with cold nature and sweet and bitter flavor enters heart, liver and stomach meridian and has the effect of clearing heat, drying dampness, killing worms and brightening eyes. Root of dried Rhemannia with cold nature and sweet and bitter flavor enters heart, liver and stomach meridian and has the effect of clearing heat, cooling blood, nourishing yin and engendering liquid due to moistening body effect from sweet flavour and cold nature and clearing heat effect from bitter flavour and cold nature. Lily bulb with cold nature and sweet flavor enters lung and heart meridian and has the effect of moistening lung, suppressing cough, cleaning heart and quieting the spirit. Among above five herbs, flower of lonicera, bamboo leaf and snake gallbladder are focus on clearing heat and removing toxin, and root of dried Rhemannia and the lily bulb are focus on nourishing yin, relieving fire, cooling blood and shrinking sore. All of the five herbs combine together to assist sovereign and ministerial components to clear heat, remove toxin, nourish yin and cooling fire as adjuvant components.

In the formula of the invention, Chinese wild ginger with warm nature and acrid flavor enters lung and kidney meridian and has the effect of dredging orifices, dissipating cold and relieving pain due to dissipating effect from acrid flavour and warm nature. The Chinese wild ginger can repress the deficiency of cool and cold nature of most herbs in the formula, and conducts the medicine out-thrusting orifices and skin, as an assistant component. With the whole components combining together the effect of clearing heat, draining fire, cooling blood and shrinking sores could be achieved.

The clinical effect of the medicament of the invention for treating Behcet's Syndrome can be enhanced when Ganoderma and thunder god vine are added, which results in rapid extinction of nodositas erythema, quick elimination of arthralgia, and prolonged catabasis. Ganoderma has the effect of strenghening body resistance, and thunder god vine has the effect of enhancing immunity. It is confirmed by the clinical observation that the cure rate of the medicament of the invention to Behcet's Syndrome is more than 90%.

The pharmacodynamic test of the medicament of the invention (which is referred to as Sanlian Tablet hereinafter) is described as the following:

The Therapy Effect of Rabbit's Ulcer in Mouth Induced by Acetic Acid

Administration: Sanlian Tablet, the medicament of the invention, 0.6 g/tablet (containing crude drugs 4.28 g/tablet);

Watermelon frost lozenges with lot number 9710025, provided by Guilin San Jin Pharmaceutical Group Co.

Model: 40 New Zealand rabbits weighing 2.0–2.5 kg, including male and female rabbits, were used. The models were made by pressing cotton sticks soaked with acetic acid in the intermediate of rabbits' tangues for about 15 seconds, the diameter of mucosal ulcer is 5 mm.

Grouping: After modeled, the rabbits were randomly divided into four groups with 10 rabbits each, among which two groups were used as treated-groups for administering the Sanlian Tablets of the invention in different dosage, one group was used as a compared treated-group for administrating Watermelon frost lozenges, and the other group was used as a control group for administering water of equal volume.

The blending suspensions used for treated-group rabbits were prepared from the extractum of the Sanlian Tablets (2.54 g crude drugs/ml) of the invention and distilled water, which concentrations were 50.4 g and 100.8 g crude drugs per 100 ml respectively. Watermelon frost lozenges were grinded, and then were prepared with distilled water into a liquid with 157 g drug/100 ml, which was used by the rabbits of the compared treated-group.

The administrating dosage of the Sanlian Tablets is 5.04 g and 10.08 g crude drugs/kg and that of Watermelon frost lozenges is 15.7 g/kg.

The rabbits of the treated-groups and the compared treated-group were administered according to above said dosages, while the rabbits of the control group were administered water of equal water. The method of administering was filling the liquid into stomach, once a day for continuous 7 days. The symptoms of topical red and swollen, the amount of exudate, and the healed time of ulcer were observed everyday. These rabbits were killed at the eighth day, their tongues were taken for visional observation at first, then for pathological section observation.

The results indicated that from the white ulcer formed after the rabbits modeled, white secretion occurred at the next day. During observation, the white secretion in the rabbits of the control group were obviously more than that in the other groups, the secretion in the groups administered (including the treated-groups and the compared treated-group) were decreased distinctly at the third day, the area of ulcer were apparently shrunk. The animals were killed after the end of administering, and the observation results are listed in following Table 1 and 2.

TABLE 1

The therapy effect of Sanlian Tablets on treating the rabbits' ulcer in mouth induced by acetic acid (x ± SD, n = 10) (visional observation)

| group | Dosage (g/kg) | amount of dead rabbit | survival ratio (%) | area of ulcer (mm$^2$) | amount of cured rabbit | cure rate (%) |
|---|---|---|---|---|---|---|
| Control group | Water | 3 | 70 | 62.6 ± 13.4 | 0 | 0 |
| compared treated-group | 15.7 | 1 | 90 | 11.7 ± 6.2*** | 7 | 70*** |
| treated-group | 5.04 | 0 | 100 | 8.6 ± 3.4*** | 8 | 80*** |
| treated-group | 10.08 | 0 | 100 | 0 ± 0*** | 10 | 100*** |

Note: Comparing with the control group, the groups marked with *** has P less than 0.01.

In above observation, the standard of cure is that no redness and swilling or secretion, and no apparent ulcer or colored were observed at the site of modeled.

TABLE 2

The therapy effect of the Sanlian Tablets on rabbits' ulcer in mouth induced by acetic acid (x ± SD, n = 10) (examined by pathological methods)

| Group | Dosage (g/kg) | Amount of sample (number) | ulcer | Erosion | inflammation of part focus | normal |
|---|---|---|---|---|---|---|
| Control group | water | 10 | 8 | 1 | 1 | 0 |
| compared treated-group | 15.7 | 10 | 2 | 1 | 0 | 7*** |
| treated-group | 5.04 | 10 | 1 | 0 | 1 | 8*** |
| treated-group | 10.08 | 10 | 0 | 0 | 1 | 9*** |

Note: Comparing with the control group, for the group marked with * P > 0.05 for group with  P < 0.05, for group with * P < 0.01

As shown in the results, according to visional obversation and examination of pathological section, Sanlian Tablets of the invention have remarkable therapy effect on the ulcer in mouth induced by acetic acid as compared with that of the control group and the compared treated-group.

Clinical Pharmacodynamic Observation of Said Medicament According to the Invention The medicament of the invention were clinically observed by the Department of Stomatology of First Hospital of Hunan Chinese Medicine College, the result shows that its whole effective rate is 93% and marked effective rate is 57%.

Experimental example: the clinical observation for the medicament of the invention (clinically, named Sanlian Tablets) for the treatment of recurrent ulcer in mouth.

1. General Information 30 patients were treated, among which there were 7 male patients, 23 female patients, the ratio of female and male was 1:0.3. Among them 7 patients were 20 to 30 years old, 8 patients were 31 to 40 years old, 11 patients were 41 to 50 years old, 4 patients were elder than 50 years old. Among these patients there were 10 professional cadres, 7 teachers, 8 workers, 3 drivers, 1 peasant and 1 student respectively.

2. Diagnostic Stardard 2.1 Diagnostic Stardard of Traditional Chinese Medicine

Most of the ulcer in mouth appeared around the root of the tongue. The ulcer was fewer and small, and the surface of the ulcer was gray white. The peripheral mucosa was slight red and swollen. One ucler cureds and then another rised, and the situation went on continually. There may be accompanied by dry throat and tongue, limp aching lumbus and knees, red tongue, reduced tongue fur, and fine and rapid pulse.

2.2 Diagnostic Stardard of Western Medicine 2.2.1 The ulcer occurred repeatly, its intermittent period was indefinite, one ulcer cured and another rised in serious patient, and the course of disease is self-restrictive.

2.2.2 Most of the ulcer occurred on the oral area covered by mucosa, such as lip, tongue, cheek, bottom of mouth and soft palate. The ulcer appeared as round or ellipse and dented down, and its surface was covered by light yellow false mucosa. Clininally, the ulcer could be classified into three types.

Light type aphtta: Its diameter was about 2–3 mm, the number of ulcer was fewer. Generally, it could be healed in 1 to 2 weeks, no scar remained when healed.

Stomatitis type aphtta: The number of ulcer could approximate to teen and tens, there may be accompanied by general symptom such as fever.

Periglandular aphtta: Its diameter was about 5–20 mm, the ulcer could reach to the mucomembranous gland. The course of disease could be about several weeks to several months, there were scar remained when healed.

3. Clinical Test 3.1 Treatment Method

The medicament of the invention could be administered thrice every day, 3 tablets once, one course of treatment is half month, the patients were serially administered by two courses of treatment.

3.2 Observation Items 3.2.1 General information: It includes name, sex, age, profession, diagnose by western medicine, diagnose of traditional Chinese medicine, syndrome identification by traditional Chinese medicine, course of disease, history of disease, induced factor, present symptom, tongue image and pulse image etc.

3.2.2 Major symptom: Most of the ulcer in mouth appeared around the root of the tongue, the number of ulcer was fewer and the area of ulcer was small. The surface of the ulcer was gray white, the peripheral mucosa was slight red and swollen. One surface of the ucler rised after another was cured, and the situation went on continually. There may be accompanied by dry throat and tongue, limp aching lumbus and knees, red tongue, reduced tongue fur, and fine and rapid pulse.

3.2.3 Side effect: Mainly observed gastro-intestinal reaction, nausea, vomit, diarrhoea, allergic reaction, etc.

3.2.4 Observation method of curative effect: The major symptoms were classified into four grades by a grading method according to the degree of slight and severe, including slight grade(+), mild grade(++), severe grade(+++), serious grade(++++), every symbol "+" was recorded as 1 score, the disappearance of symptoms was recorded as "0" score, the pulse image and tongue image conformed to the stardard of syndrom identification was recorded as 1 to 4 scores.

4. Stardard of Evalutaing Curative Effect 4.1 Notable effect: It means that the intermittent period was prolonged after treatment of every type aphtta, there was no recurrence in 3 months upon observation.

4.2 Improved effect: It means that three indexes of the following five indexes were achieved for the patient, i.e. healed time was quickened, the intermittent period was prolonged, the degree of pain was relieved, the number of ulcer was reduced, and the diameter of ulcer was shrunk.

4.3 Invalid effect: It means that patients couldn't reach the standard of improved effect.

5. In the Experiment the Matters Below Were Followed Strictly 5.1 No any other treatment medicaments were added during treating.

5.2 The observation table was filled in conscientiously according to the scientific research design.

5.3 The symptom and sign should be recorded once before administered, and recorded again respectively at the 3th day, 6th day, 9th day, and the end of one month during administering.

5.4 The side effect of the medicament was recorded strictly according to the facts.

6. Results of Treatment are Listed in Tables 3 and 4.

TABLE 3

The observation of curative effect after the treatment

| | Cure rate | | | | | | |
|---|---|---|---|---|---|---|---|
| | notable effect | | improved effect | | invalid | | effective |
| days | case number | notable effect % | case number | Improved effect % | case number | invalid % | rate (%) |
| 3 | 0 | | 24 | 80 | 6 | 20 | 80 |
| 6 | 9 | 3 | 18 | 60 | 3 | 10 | 90 |
| 9 | 17 | 56.6 | 10 | 33.33 | 3 | 10 | 90 |
| 1 month | 17 | 56.6 | 10 | 33.33 | 3 | 10 | 90 |

TABLE 4

The improved condition of the symptoms at the end of one month after the treatment

| | dry throat and mouth | limp aching lumbus and knees | dizzy head and tinnitus | insomnia and profuse dreaming |
|---|---|---|---|---|
| before the treatment (case number) | 28 | 15 | 19 | 27 |
| after the treatment (case number) | 13 | 14 | 10 | 26 |
| whole effective rate (%) | 53.57 | 6.67 | 47.37 | 3.70 |

7. Concluding Remarks

Recurrent ulcer in mouth is a common disease and frequently-occurring disease in department of stomatology. After 30 cases were treated with the Sanlian Tablets for 4 months, the results indicated that there were 17 cases with notable effect, 10 cases with improved effect, 3 cases with invalid effect, the improved rate was 33.33%, the whole effective rate was 90%, the curative effect was satisfied.

DETAILED DESCRIPTION OF THE PREFERRED EMBODIMENT

EXAMPLE 1

Each raw material herb was weighed according to the following weight proportion:

| | |
|---|---|
| root of Coptis chinesis | 7.5 g |
| Isatis root | 4.5 g |
| flower lonicera | 4.5 g |
| puccoon | 3 g |
| root dried Rhemannia | 6 g |
| bamboo leaf | 4.5 g |
| corydalis bungeana | 4.5 g |
| Chinese wild ginger | 3 g |
| lily bulb | 4.5 g |
| snake gallbladder (dried powder) | 0.3 g |

The medicament of the invention was prepared in the following way.

The raw materials, bamboo leaf, root of *Coptis chinesis*, Isatis root, flower of lonicera, *Corydalis bungeana*, Lily bulb, root of dried Rehmannia of the above mentioned portions were decocted twice with water, in which the amount of water added was 8-fold that of the herbs and decocting was kept for 1.5 hours for the first decocting, and the amount of water added was 6-fold that of the herbs and decocting was kept for one hour for second decocting. Two decoction liquids obtained above are combined for later use. Chinese wild ginger in the said portions is decocted twice with 3-fold water each time by a common method, volatile oil was collected for later use and then the decoction liquid was combined with the liquid obtain from above seven raw materials, and next concentrated into an extractum which specific gravity maight be 1.35. The extractum was added with 90–95% ethanol. The mixture was stirred and concentrated whiling recovering ethanol and dried at 45–50° C. to yield dried extractum 3.9 g. Puccoon in said portions was extracted with 90–95% ethanol under reflux, and the extracted liquor was concentrated while recovering ethanol and dried at 50° C. to obtain dried extractum 0.18 g. The dried extractum was combined with the dried extractum from above mixture, mixed with snake gallbladder powder, then grinded into powder, and added with a common assistant additive, prepared into granule, dried, sprayed with the volatile oil of Chinese wild ginger obtained above, and then prepared into tablets by tabletting.

EXAMPLE 2

Each raw material herb was weighed according to the following weight proportion:

| | |
|---|---|
| root of Coptis chinesis | 7.5 g |
| Isatis root | 4.5 g |
| flower lonicera | 4.5 g |
| puccoon | 3 g |
| root of dried Rhemannia | 6 g |
| bamboo leaf | 4.5 g |
| corydalis bungeana | 4.5 g |
| Chinese wild ginger | 3 g |
| lily bulb | 4.5 g |
| snake gallbladder (dried powder) | 0.3 g |
| ganoderma | 6 g |
| thunder god vine | 1.5 g |

The medicament of the invention was prepared in the following way.

The raw materials, bamboo leaf, root of *Coptis chinesis*, Isatis root, flower of lonicera, *Corydalis bungeana*, Lily bulb, root of dried Rehmannia, ganoderma and thunder god vine of the above mentioned portions were decocted twice with water, in which the amount of water added was 8-fold that of the herbs and decocting was kept for 1.5 hours for first decocting, and the amount of water added was 6-fold that of the herbs and decocting was kept for one hour for second decocting. Two decoction liquids obtained above are combined for later use. Chinese wild ginger in the said portions is decocted twice with 3-fold water each time by a common method, volatile oil was collected for later use and then the decoction liquid was combined with the liquid obtain from above raw materials, and next concentrated into an extractum which specific gravity maight be 1.35. The extractum was added with 90–95% ethanol. The ethanol solution was stirred and concentrated whiling recovering ethanol and dried at 45–50° C. to yield dried extractum 3.9 g. Puccoon in said portions was extracted with 90–95% ethanol under reflux, and the extracted liquor was concentrated while recovering ethanol and dried at 50° C. to obtain dried extractum 0.18 g. The dried extractum was combined with the dried extractum from above mixture, mixed with snake gallbladder powder and then grinded into powder, added with a common assistant additive, prepared into granule, dried, sprayed with the volatile oil of Chinese wild ginger obtained above, and then prepared into tablets by tabletting.

Each raw material herb was weighed by the same weight proportion of example 1, and then prepared into a formulated medicament in the same manner as example 1, then 6 g of ganoderma and 1.5 g of thunder god vine were added into said formulated medicament. The medicament of the invention prepared has effect of strenghening body resistance and eliminating evil, and enhancing curative effect.

INDUSTRIAL APPLICABILITY

The medicament for treating recurrent ulcer in mouth and Behcet's Syndrome according to the invention, has the effect of clearing heat and draining fire, dimishing inflammation, antibiosis, cooling blood and shrinking sores, etc. It was demonstrated that the medicament according to the invention has a notable effect for treatment of ulcer in mouth by animal trials and clinical pharmacodynamic observation to the patients. The cure rate of ulcer in mouth was 80–100% and the cure rate of Behcet's Syndrome could be approximately more than 90%. Thus the medicament of the invention is an effective medicament of widespread use, rapid effect and high cure rate.

What is claimed is:

1. A medicament for treating any of a mouth ulcer and Behcet's Syndrome, comprising: root of *Coptis chinesis*, root of Isatis, flower of Lonicera, Puccoona, root of Rehmannia, leaf of bamboo, *Corydalis bungeana*, Chinese wild ginger, bulb of Lily and snake gall bladder.

2. The medicament according to claim 1, wherein the Rehmannia and the snake gall bladder are dried.

3. The medicament according to claim 2, wherein the relative proportions of the medicament are: root of *Coptis chinesis*, 6–9 parts, root of Isatis, 2–5 parts, flower of Lonicera, 2–5 parts, Puccoon, 2–4 parts, root of Rehmannia, 3–8 parts, leaf of bamboo, 3–6 parts, *Corydalis bungeana*, 2–5 parts, Chinese wild ginger, 2–4 parts, bulb of Lily, 2–5 parts, and snake gall bladder, 0.1–0.5 parts.

4. The medicament according to claim 3, wherein the relative proportions are: root of *Coptis chinesis*, 7.5 parts, root of Isatis, 4.5 parts, flower of Lonicera, 4.5 parts, Puccoon, 3 parts, root of Rehmannia, 6 parts, leaf of bamboo, 4.5 parts, *Corydalis bungeana*, 4.5 parts, Chinese wild ginger, 3 parts, bulb of Lily, 4.5 parts, and snake gall bladder, 0.3 parts.

5. The medicament according to claim 1, further comprising: ganoderma and thunder god vine.

6. The medicament according to claim 5, wherein the relative proportion in unit weight of ganoderma and thunder god vine in the medicament is for ganoderma 3 to 8 parts and for thunder god vine, 1 to 3 parts.

7. The medicament according to claim 6, wherein the relative proportions in unit weight of ganoderma is 6 parts and the amount of the thunder god vine is 1.5 parts.

8. A method for preparing the medicament of claim 1, comprising:
   (a) preparing a first mixture comprising leaf of bamboo, root of *Coptis chinesis*, root of Isasis, flower of Ionicera, *Corydalis bungeana*, bulb of Lily and root of dried Rehmannia; decocting the mixture twice with water and combining and filtering the two resulting decoction liquids to obtain a filtrate;
   (b) preparing an extract of Chinese wild ginger; and Puccoon; and
   (c) combining (a) and (b) to form a second mixture.

9. A method according to claim 8, wherein the extract of Chinese wild ginger is prepared by
   decocting the Chinese wild ginger with water to provide a volatile oil and a decoction liquid of ginger; and combining and concentrating, in the presence of ethanol, the decoction liquid of ginger with the filtrate of (a) so as to form the extract in dried form.

10. A method according to claim 9, wherein the Puccoon is mixed with ethanol under reflux and an extracted liquor obtained, the extracted liquor being dried and mixed with the dried extract formed from the ginger and the filtrate to form a third mixture.

11. A method according to claim 10, wherein snake gall bladder extract is added to the third mixture to form a fourth mixture.

12. A method according to claim 11, wherein the snake gall bladder extract is in the form of a powder.

13. A method according to claim 12, wherein the fourth mixture is prepared in tablet form.

14. A method according to claim 10, wherein the concentration of ethanol for combining and concentrating the Chinese wild ginger and the filtrate, and the Puccoon is 90–95% ethanol, the extract being dried at 45–50° C.

15. A method according to claim 8, wherein twice decocting the first mixture includes for the first decoction, adding a volume of water that is 8 fold the volume of the first mixture for 1.5 hours and for the second decoction, adding an amount of water that is 6 fold the volume of the first mixture and decocting for 1 hour.

16. A method according to claim 8, wherein ganoderma and thunder god are added to the first mixture.

17. A method of treating a subject suffering from a mouth ulcer or Behcet's Syndrome, comprising: providing an effective dose of a medicament according to claim 1 and administering the medicament to the subject so as to treat the symptoms of the mouth ulcer or Behcet's syndrome.

* * * * *